US010564447B2

(12) United States Patent
Mitsui (10) Patent No.: US 10,564,447 B2
(45) Date of Patent: Feb. 18, 2020

(54) CONTACT LENS FOR CORRECTED-CORNEA CROSSLINKING, CORRECTED-CORNEA CROSSLINKING METHOD, AND RING-SHAPED CONTACT LENS (71) Applicant: Iwane Mitsui, Tokyo (JP)

(72) Inventor: Iwane Mitsui, Tokyo (JP)

(*) Notice: Subject to any disclaimer, the term of this patent is extended or adjusted under 35 U.S.C. 154(b) by 614 days.

(21) Appl. No.: 15/038,054

(22) PCT Filed: Nov. 17, 2014

(86) PCT No.: PCT/JP2014/080313
§ 371 (c)(1),
(2) Date: May 20, 2016

(87) PCT Pub. No.: WO2015/076215
PCT Pub. Date: May 28, 2015

(65) Prior Publication Data
US 2016/0299356 A1 Oct. 13, 2016

(30) Foreign Application Priority Data

Nov. 20, 2013 (JP) .................... 2013-240284
Oct. 10, 2014 (JP) .................... 2014-209472

(51) Int. Cl.
*G02C 7/02* (2006.01)
*G02C 7/04* (2006.01)
(Continued)

(52) U.S. Cl.
CPC ............ *G02C 7/047* (2013.01); *A61F 9/0017* (2013.01); *A61N 5/062* (2013.01); *G02C 7/021* (2013.01);
(Continued)

(58) Field of Classification Search
CPC .......... G02C 7/047; G02C 7/04; G02C 7/044; G02C 7/048; G02C 7/049; G02C 7/021; G02C 7/16; A61F 9/0017; A61F 9/013
(Continued)

(56) References Cited

U.S. PATENT DOCUMENTS 4,592,752 A    6/1986 Neefe
5,245,367 A    9/1993 Miller et al.
(Continued)

FOREIGN PATENT DOCUMENTS

ES    2406380 A1    6/2013
JP    H07-500267 A    1/1995
(Continued)

OTHER PUBLICATIONS

Jun. 2, 2016 International Preliminary Report on Patentability issued in International Patent Application No. PCT/JP2014/080313.
(Continued)

*Primary Examiner* — Jordan M Schwartz
(74) *Attorney, Agent, or Firm* — Oliff PLC (57) ABSTRACT In a contact lens for corrected-cornea crosslinking, a relief region constituted by a concave portion and a pressing region constituted by a convex portion are formed on a side of the lens in contact with a cornea of a patient. When these regions are pressed to the cornea to change a shape thereof, and a curvature of the concave curved-surface to be formed on the cornea is defined as $R_0$ and a curvature of the convex curved-surface of the pressing region is defined as $R_s$, $R_s$ is set, for example for correcting myopia, to satisfy $R_s=R_0+5.0$ D to $R_0+10.0$ D. When the contact lens having such a configuration is used for correcting the cornea and fixing the corrected state by crosslinking, the shape of the cornea can be accurately formed.

11 Claims, 8 Drawing Sheets (51) Int. Cl.
*A61F 9/00* (2006.01)
*A61N 5/06* (2006.01)
*A61F 9/013* (2006.01)
*G02C 7/16* (2006.01)

(52) U.S. Cl.
CPC ....... *A61F 9/013* (2013.01); *A61N 2005/0648* (2013.01); *G02C 7/16* (2013.01)

(58) Field of Classification Search
USPC .......................................... 351/159.23; 606/5
See application file for complete search history.

(56) References Cited

U.S. PATENT DOCUMENTS

| | | | |
|---|---|---|---|
| 5,270,051 A | 12/1993 | Harris | |
| 5,626,865 A | 5/1997 | Harris et al. | |
| 5,695,509 A * | 12/1997 | El Hage | A61F 9/013 351/159.2 |
| 5,757,458 A | 5/1998 | Miller et al. | |
| 5,786,883 A | 7/1998 | Miller et al. | |
| 5,929,968 A * | 7/1999 | Cotie | G02C 7/04 351/159.02 |
| 5,972,011 A * | 10/1999 | Pierce | A61F 9/013 128/898 |
| 6,926,406 B2 * | 8/2005 | Mitsui | G02C 7/047 351/159.79 |
| 2002/0159025 A1 | 10/2002 | Legerton et al. | |
| 2002/0186344 A1 | 12/2002 | Tung | |
| 2003/0083743 A1 | 5/2003 | Perez | |
| 2003/0095232 A1 | 5/2003 | Mitsui | |
| 2003/0105521 A1 | 6/2003 | Perez | |
| 2003/0220653 A1 | 11/2003 | Perez | |
| 2004/0070732 A1 | 4/2004 | Mitsui | |
| 2005/0070942 A1 | 3/2005 | Perez | |
| 2006/0126015 A1 | 6/2006 | Legerton et al. | |
| 2006/0152673 A1 | 7/2006 | Cotie et al. | |
| 2007/0296915 A1 | 12/2007 | Legerton et al. | |
| 2008/0212020 A1 | 9/2008 | Legerton et al. | |
| 2009/0171305 A1 | 7/2009 | El Hage | |
| 2010/0039620 A1 | 2/2010 | Legerton et al. | |
| 2010/0073635 A1 | 3/2010 | Legerton et al. | |
| 2011/0166535 A1 | 7/2011 | Hasegawa et al. | |
| 2011/0237999 A1 | 9/2011 | Muller et al. | |
| 2011/0288466 A1 | 11/2011 | Muller et al. | |
| 2012/0215155 A1 | 8/2012 | Muller et al. | |
| 2012/0268711 A1 * | 10/2012 | Lai | G02C 7/047 351/159.15 |
| 2012/0283621 A1 | 11/2012 | Muller | |
| 2012/0289886 A1 | 11/2012 | Muller et al. | |
| 2013/0211389 A1 | 8/2013 | Chuck et al. | |
| 2014/0043588 A1 | 2/2014 | Grant et al. | |

FOREIGN PATENT DOCUMENTS

| | | |
|---|---|---|
| JP | H09-502542 A | 3/1997 |
| JP | 2000-298251 A | 10/2000 |
| JP | 2003-144479 A | 5/2003 |
| JP | 2004-504627 A | 2/2004 |
| JP | 2004-517345 A | 6/2004 |
| JP | 2006-043150 A | 2/2006 |
| JP | 3881221 B2 | 2/2007 |
| JP | 2013-518672 A | 5/2013 |
| JP | 2013-521988 A | 6/2013 |
| WO | 2009/090763 A1 | 7/2009 |
| WO | 2009/149116 A2 | 12/2009 |
| WO | 2013/052511 A2 | 4/2013 |

OTHER PUBLICATIONS

Jul. 27, 2017 Search Report issued in European Patent Application No. 14863215.1.
Mar. 3, 2015 International Search Report issued in International Patent Application No. PCT/JP2014/080313.

* cited by examiner

Related Art

FIG. 8

Related Art

CONTACT LENS FOR CORRECTED-CORNEA CROSSLINKING, CORRECTED-CORNEA CROSSLINKING METHOD, AND RING-SHAPED CONTACT LENS

TECHNICAL FIELD

The present invention relates to a contact lens for corrected-cornea crosslinking that changes a shape of the cornea of a patient while being mounted for a given period of time and fixes the shape thereof in a state of correcting myopia, hyperopia, astigmatism, or keratoconus cornea, and a corrected-cornea crosslinking method.

Further, the present invention relates to a ring-shaped contact lens, a ring-shaped cornea-correction contact lens, and a ring-shaped color contact lens, which include a through hole at a portion corresponding to the central area of a corneal dome or the pupil, and, in particular, a ring-shaped cornea-correction contact lens that changes a shape of the cornea of a patient while being mounted for a given period of time, thereby causing a state of correcting hyperopia, and a corrected-cornea crosslinking method and a color contact lens for dress up using the same.

BACKGROUND ART

For example, the inventor proposes, in Patent Literature 1, a contact lens for changing a shape of the cornea of a patient by being mounted during sleep and the like, and correcting myopia and/or astigmatism at the time when the contact lens is removed. Subsequently, the inventor has also developed a similar contact lens for correcting hyperopia.

Figure 7:
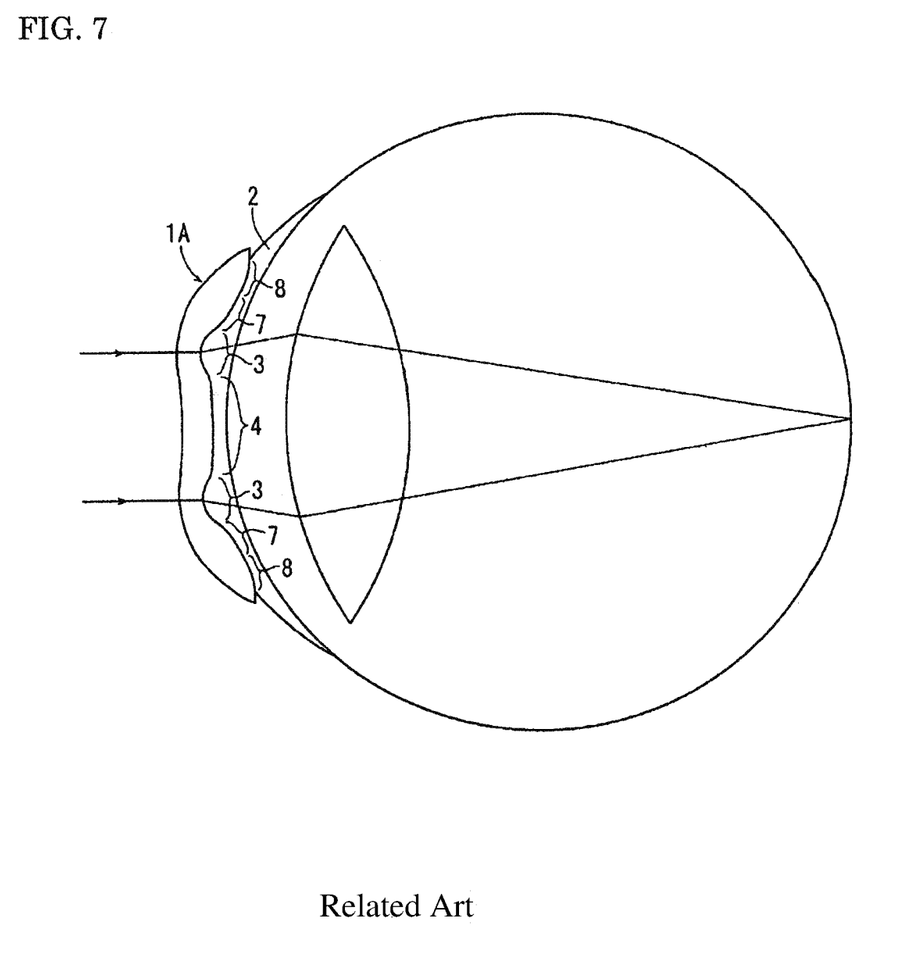
FIG. 7 is a cross-sectional view schematically illustrating a conventional contact lens for correcting myopia, shown together with a part of the cornea and the eyeball.

As shown in FIG. 7, in a contact lens 1A for correcting myopia as described above, a relief region 3 constituted by a concave portion and a pressing region 4 constituted by a convex portion are formed on a side of the lens in contact with a cornea 2 of a patient. By pressing the relief region 3 and the pressing region 4 to the cornea 2, a part of the cornea is pushed downward by the pressing region 4 and, as a reaction thereof, a part of the cornea 2 is projected into the relief region 3, so that the cornea 2 is corrected into a shape in which desirable naked eye vision can be obtained or a shape in which keratoconus cornea is smoothly suppressed.

Figure 8:
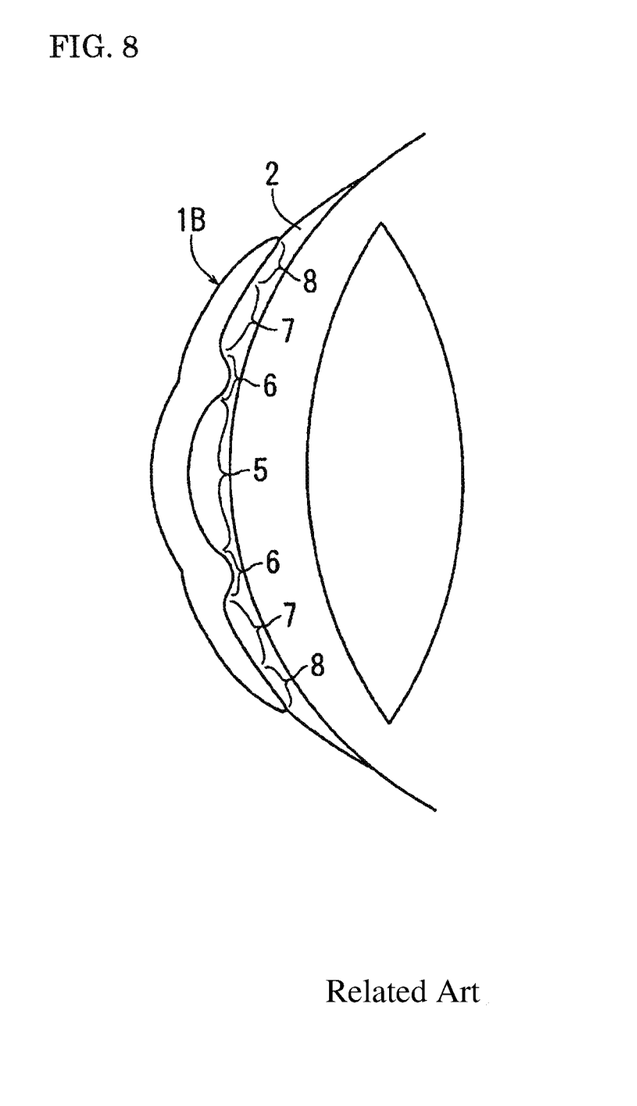
FIG. 8 is a cross-sectional view schematically illustrating a conventional contact lens for correcting hyperopia, shown in the same manner as FIG. 7.

As shown in FIG. 8, in a contact lens 1B for correcting hyperopia, a relief region 5 and a pressing region 6 are reversed to each other as compared to the case of correcting myopia.

In the contact lens 1A for correcting myopia, the pressing region 4 is formed to project in a convex curved-surface shape at a position corresponding to the center of the corneal dome to be pressed when the contact lens 1A is mounted on the cornea 2. In contrast, the relief region 3 is constituted by an annular concave portion that has a cross section in a concave circular arc shape at a position encircling the outer periphery of the pressing region 4, and configured such that a part of the cornea 2 enters the annular concave portion thereof as a reaction of the cornea 2 pushed downward by the pressing region 4. The contact lens 1A also includes an anchor region 7 having a shape aligned with a contour of the cornea 2, when the contact lens 1A is mounted on the cornea 2, at a position encircling the outer periphery of the relief region 3, and a peripheral portion 8 further encircling the outer periphery of the anchor region 7.

When the above-mentioned contact lenses 1A and 1B are not put on for a long period, myopia or hyperopia is returned to its original condition by a restoring force of the cornea, thus it is desirable that the cornea be fixed in a corrected state.

On the other hand, there has been known a refraction correction surgery in which a corneal tissue in a state of being infiltrated with riboflavin (vitamin B2) is irradiated with ultraviolet rays for crosslinking collagens constituting the cornea to one another, thereby enhancing strength of the cornea and fixing the cornea.

It is expected that a shape of the cornea can be fixed to some extent in a state of being corrected by a contact lens by combining this crosslinking method and the above-mentioned contact lenses (publicly unknown).

However, although the above-described crosslinking can suppress the progress of keratoconus cornea of a patient, eyesight varies after the crosslinking and it is difficult to correct eyesight to be normal. As such, it is speculated that there is a high probability of being unable to recover eyesight as aimed even when the above-mentioned contact lenses for correction are used.

Further, apart from the contact lens for vision correction, there is a color contact lens for dress up.

This color contact lens for dress up is composed of a central portion corresponding to the pupil and an annular portion arranged on the outside thereof. The annular portion is applied with annular coloring while the central portion is uncolored, and this contact lens does not have an eyesight correcting function.

The conventional contact lens for vision correction or the color contact lens for dress up have, for example, such problems that they cannot be used in the case of diseases such as dry eye and that the center of these lenses is shifted from a position of the pupil during the wearing thereof. Further, a portion of the lens corresponding to the central portion of the corneal dome or the pupil needs to be transparent, and thus there is a problem that a 3D printer forming a final product in an opaque state cannot be used for forming the lens.

CITATION LIST

Patent Literature

Patent Literature 1: Japanese Patent No. 3881221

SUMMARY OF INVENTION

Technical Problem

An object of the present invention is to provide a contact lens for corrected-cornea crosslinking and a corrected-cornea crosslinking method capable of accurately correcting the cornea using the contact lens for correcting vision or astigmatism through the analysis of the behavior of the cornea of which strength is enhanced by the crosslinking, and fixing the cornea in the corrected state.

Solution to Problem

Further, another object of the present invention is to provide a ring-shaped contact lens, a ring-shaped cornea-correction contact lens, a corrected-cornea crosslinking method, and a color contact lens for dress up, wherein a contact lens for correcting vision and a color contact lens for dress up can be used in a case of dry eye by allowing supply of oxygen and a lacrimal fluid to the surface of the central portion of the corneal dome, can be formed of an opaque material, and can be prevented from being shifted from a position having the pupil as a center.

The inventor has found, as a result of his/her earnest studies, that the cornea of which strength is enhanced by the crosslinking is projected forward by an elastically restoring force of the eyeball and invented a contact lens for corrected-cornea crosslinking and a corrected-cornea crosslinking method capable of achieving aimed naked eye vision by taking this restoring force into consideration.

Further the inventor has found, as a result of his/her earnest studies, that the relief region is not necessarily brought into contact with the cornea in correcting the cornea for hyperopia and presbyopia and that a color contact lens for dress up may have a portion corresponding to the pupil formed in a so-called transparent state, thereby developing a ring-shaped cornea-correction contact lens and a ring-shaped color contact lens for dress up having a central portion formed as a through hole.

In summary, the above-described objectives are achieved by the following aspects of the present invention.

(1) A contact lens for corrected-cornea crosslinking, comprising a relief region constituted by a concave portion and a pressing region constituted by a convex region, each being formed on a side of the contact lens in contact with a cornea of a patient, the contact lens being for correcting at least one of naked eye vision and keratoconus cornea by pressing the relief region and the pressing region to the cornea and changing a shape thereof, wherein: when the contact lens is mounted on the cornea, the pressing region is projected in a convex curved-surface shape at a position corresponding to a center of a corneal dome to be pressed, thereby forming a concave curved-surface on the cornea; and the relief region is constituted by an annular concave portion that has a cross section in a concave circular arc shape, the relief region being formed at a position encircling an outer periphery of the pressing region, the contact lens further comprising: an anchor region having a shape aligned with a contour of the cornea when the contact lens is mounted on the cornea, the anchor region being provided at a position encircling an outer periphery of the relief region; and a peripheral portion encircling an outer periphery of the anchor region, wherein the contact lens is configured such that, when a curvature of the concave curved-surface to be formed on the cornea is defined as $R_0$ and a curvature of the convex curved-surface of the pressing region is defined as $R_s$, $R_s$ is set to satisfy $R_s=R_0+5.0$ D to $R_0+10.0$ D.

(2) A contact lens for corrected-cornea crosslinking, comprising a relief region constituted by a concave portion and a pressing region constituted by a convex region, each being formed on a side of the contact lens in contact with a cornea of a patient, the contact lens being for correcting at least one of naked eye vision and keratoconus cornea by pressing the relief region and the pressing region to the cornea and changing a shape thereof, wherein: when the contact lens is mounted on the cornea, the relief region is formed in a concave curved-surface shape at a position being in contact with a center of a corneal dome, thereby forming a convex curved-surface on the cornea; and the pressing region is constituted by an annular convex portion that has a cross section in a convex circular arc shape, the pressing region being formed at a position encircling an outer periphery of the relief region, the contact lens further comprising: an anchor region having a shape aligned with a contour of the cornea when the contact lens is mounted on the cornea, the anchor region being provided at a position encircling an outer periphery of the pressing region; and a peripheral portion encircling an outer periphery of the anchor region, wherein the contact lens is configured such that, when a curvature of the convex curved-surface to be formed on the cornea is defined as $r_0$ and a curvature of the concave curved-surface of the relief region is defined as $r_s$, $r_s$ is set to satisfy $r_s=r_0-6.5$ D to $r_0-11.5$ D.

(3) A corrected-cornea crosslinking method comprising: a step of infiltrating a riboflavin solution into a corneal tissue; a step of mounting the contact lens for corrected-cornea crosslinking according to any of claims 1 to 5 on the cornea after infiltration of the riboflavin in such a manner that the cornea is pressed by the pressing region and a part of the cornea pressed by deformation of the cornea that is pressed enters the relief region; and a step of irradiating, while the contact lens for corrected-cornea crosslinking is mounted on the cornea, the cornea with ultraviolet rays via the contact lens for corrected-cornea crosslinking, thereby crosslinking collagen fibers that constitute the cornea.

(4) A ring-shaped contact lens comprising a through hole at a portion thereof corresponding to a pupil during wearing of the lens.

(5) A ring-shaped cornea-correction contact lens, comprising a relief region constituted by a concave portion and a pressing region constituted by a convex region, each being formed on a side of the contact lens in contact with a cornea of a patient, the cornea-correction contact lens being for correcting at least one of hyperopia or presbyopia by pressing at least the pressing region to the cornea and changing a shape thereof, wherein: when the contact lens is mounted on the cornea, the relief region is formed as a through hole at a position corresponding to a central area of a corneal dome, so that the cornea is projected into the through hole to form a convex curved-surface; and the pressing region is constituted by an annular convex portion having a cross section in a convex circular arc shape, the pressing region being formed at a position encircling an outer periphery of the relief region, the cornea-correction contact lens further comprising at least an anchor region of: an anchor region having a shape aligned with a contour of the cornea when the lens is mounted on the cornea, the anchor region being provided at a position encircling an outer periphery of the pressing region; and a peripheral portion encircling an outer periphery of the anchor region.

(6) A corrected-cornea crosslinking method comprising: a step of infiltrating a riboflavin solution into a corneal tissue; a step of mounting the ring-shaped cornea-correction contact lens described in (4) or (5) on the cornea after infiltration of the riboflavin in such a manner that the cornea is pressed by the pressing region and a part of the cornea pressed by deformation of the cornea that is pressed enters the relief region; and a step of irradiating, while the ring-shaped cornea-correction contact lens is mounted on the cornea, the cornea with ultraviolet rays via the through hole, thereby crosslinking collagen fibers that constitute the cornea.

(7) A color contact lens for dress up, comprising: a through hole at a portion thereof corresponding to a pupil of a wearer; and an annular coloring portion at its periphery.

Advantageous Effects of Invention

The contact lens for corrected-cornea crosslinking according to the present invention provides an advantageous effect that a shape of the cornea after crosslinking can be accurately set so as to be capable of recovering aimed eye vision by setting a concave part and a convex part of the contact lens for deforming the cornea in consideration of corneal deformation (spring back) occurring after crosslinking based on the elastically restoring force of the eyeball in advance.

Further, since the ring-shaped contact lens according to the present invention has a central portion corresponding to the central area of the corneal dome or the pupil formed as a through hole when being mounted and thus provides such advantageous effects that the contact lens can be used in the case of dry eye by allowing supply of oxygen and a lacrimal fluid to the surface of the central portion of the corneal dome, can be formed of an opaque material, and can also be prevented from being shifted from a position having the pupil as a center.

DESCRIPTION OF EMBODIMENTS

In the contact lens according to the present embodiment, a relief region constituted by a concave portion and a pressing region constituted by a convex portion are formed on a side of the lens in contact with the cornea of a patient. By pressing the relief region and the pressing region to the cornea, a part of the cornea is pushed downward by the pressing region and, as a reaction thereof, a part of the cornea is projected into the relief region, so that the cornea is corrected into a shape in which desirable naked eye vision can be obtained or a shape in which keratoconus cornea is smoothly suppressed. When the contact lens is removed after corneal deformation is fixed by crosslinking in this state, a return of deformation occurs due to spring back of the cornea. Thus, a curvature of the curve of the convex portion or the concave portion is set anticipating this return in advance.

The feature of the present invention is that, in the case of correcting myopia, when a curvature of the concave curved-surface to be formed on the cornea is defined as $R_0$ and a curvature of the convex curved-surface of the pressing region is defined as $R_s$, $R_s$ is set to satisfy $R_s=R_0+5.0$ D to $R_0+10.0$ D.

In this formula, the above-mentioned values of +5.0 D to +10.0 D are a correction amount obtained by taking into consideration corneal deformation (spring back) after crosslinking based on the elastically restoring force of the eyeball, and deduced from a large number of treatment cases performed by the inventor.

The above-mentioned values are determined as follows: when the cornea of a patient is pressed at the pressing region of curvature $R_0$ and then the pressing is released, the curvature $R_s$ is obtained as $R_s=R_0+\Delta R$ where $\Delta R$ is a spring back amount at the central area of a corneal dome due to the elastically restoring force of the eyeball.

Furthermore, another feature of the present invention is that, in the case of correcting hyperopia, the pressing region and the relief region are reversed to those of the case of correcting myopia, and the feature thereof is that, when a curvature of the convex curved-surface to be formed on the cornea is defined as $r_0$ and a curvature of the concave curved-surface of the relief region is defined as $r_s$, $r_s$ is set to satisfy $r_s=r_0-6.5$ D to $r_0-11.5$ D. Also in this formula, the above-mentioned values of −6.5 D to −11.5 D are deduced from treatment cases.

Also in the case of correcting hyperopia, the above-mentioned values are based on the fact that, when a spring back amount at the central area of the corneal dome due to the elastically restoring force of the eyeball is defined as $\Delta r$, the curvature $r_s$ is obtained by $r_s=r_0-\Delta r$.

Further, it is preferred that, in the contact lens for corrected-cornea crosslinking, the outer diameter $D_1$ of a peripheral portion be set larger than an average outer diameter $D_0$ of the outer peripheral edge of the human cornea by 3.0 mm to 5.0 mm, and that a UV-shielding membrane for shielding ultraviolet rays be provided to the lens in an annular region, on a side in contact with the cornea, from a position having a diameter of $D_0$—3.0 mm to $D_0$—5.0 mm to the outermost periphery in the peripheral portion.

When the outer peripheral edge of the cornea (corneal limbus) where pluripotent cells lie is crosslinked by ultraviolet ray irradiation during crosslinking, it becomes difficult to regenerate the cornea. The UV-shielding membrane prevents this from occurring.

As a material of the UV-shielding membrane for shielding ultraviolet rays, a material harmless to the cornea, for example, a gold thin film, a titanium thin film, a silver thin film, and the like may be used.

When the UV-shielding membrane is provided outside the contact lens, ultraviolet rays incident on the central area of the contact lens are reflected/diffracted inside and sometimes reach the outer peripheral edge of the cornea. Thus, the UV-shielding membrane is provided on the side in contact with the cornea.

Further, in the ring-shaped cornea-correction contact lens according to another present embodiment, a relief region constituted by a concave portion and a pressing region constituted by a convex portion are formed on a side of the lens in contact with the cornea of a patient of hyperopia or presbyopia. By pressing the relief region and the pressing region to the cornea, a part of the cornea is pushed downward by the pressing region and, as a reaction thereof, a part of the cornea is projected into the relief region, so that the cornea is corrected into a shape in which desirable naked eye vision can be obtained. The relief region has a central area corresponding to the central area of the corneal dome formed as a through hole, into which a part of the cornea pressed by the pressing region is to be projected.

Example 1

Figure 1:
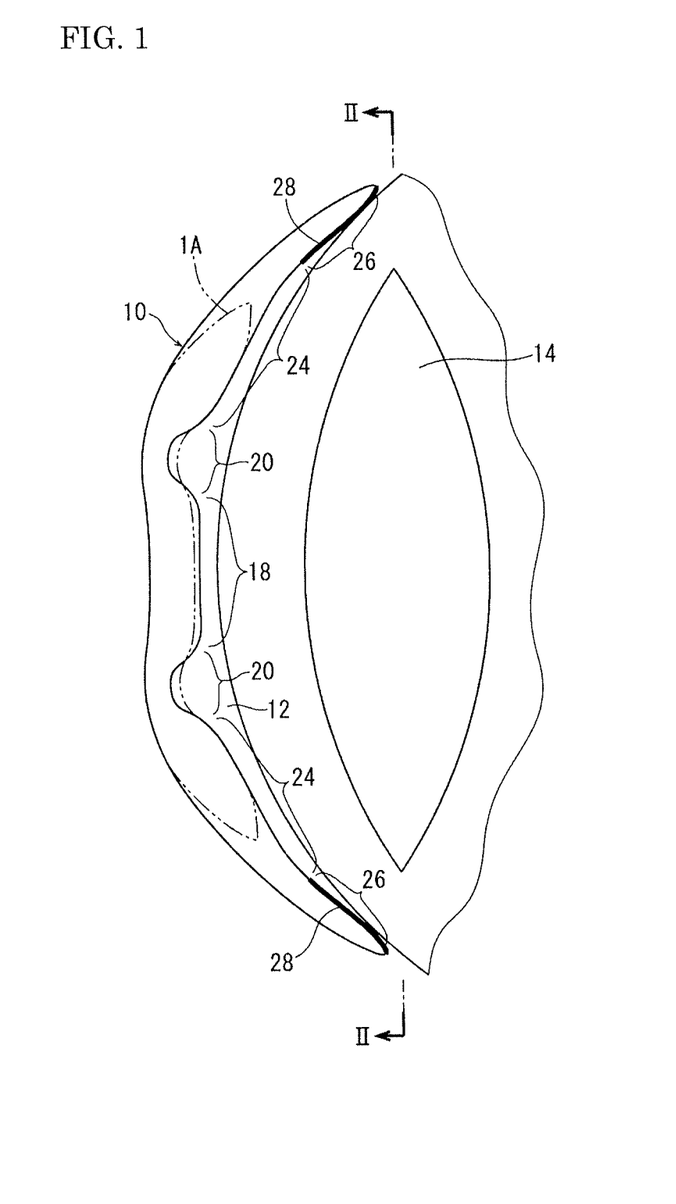
FIG. 1 is a cross-sectional view schematically illustrating a contact lens for corrected-cornea crosslinking according to Example 1 of the present invention.

As shown in FIG. 1, a contact lens 10 for correcting myopia according to Example 1 of the present invention is used by being mounted on a cornea 12. Reference numeral 14 in FIG. 1 denotes a crystalline lens.

The contact lens 10 for correcting myopia is configured to include: a pressing region 18 formed to project in a convex curved-surface shape at a position corresponding to the center of a corneal dome (a front end surface of the cornea having the most protruding portion) to be pressed; a relief region 20 constituted by an annular concave portion having a cross section in a concave circular arc shape, the relief region 20 being formed at a position encircling the outer periphery of the pressing region 18; an anchor region 24 having a shape aligned with a contour 22 (see FIG. 2) of the cornea when the contact lens is mounted on the cornea 12, the anchor region 24 being provided at a position encircling the outer periphery of the pressing region 18; and a peripheral portion 26 encircling the outer periphery of the anchor region 24.

In FIG. 1, a conventional contact lens (hereinafter referred to as a conventional lens) 1A for correcting myopia, shown in FIG. 7, is shown by a two-dot chain line.

In the contact lens 10 for correcting myopia according to Example 1, as shown by a solid line in FIG. 1, the pressing region 18 is projected towards a direction of the cornea 12 as compared to the conventional lens 1A, and conversely the relief region 20 is formed as a deeper annular concave portion than a relief region 3 of the conventional lens 1A. Furthermore, the peripheral portion 26 is larger than a peripheral portion 8 and extended along the contour of the cornea 12.

In this configuration, when a curvature of the convex curved-surface of the pressing region 18 in Example 1 is defined as $R_s$ and a curvature of the convex curved-surface of the conventional lens 1A is defined as $R_0$, $R_s$ is set to satisfy $R_s = R_0 + 5.0$ D to $R_0 + 10.0$ D.

The aforementioned curvature $R_0$ is a curvature of a concave curved-surface to be formed on the cornea 12 for correcting at least one of naked eye vision and keratoconus cornea of a patient. The reason why $R_s$ is set to satisfy $R_s > R_0$ is that when the cornea of a patient is pressed by the pressing region having a convex curved-surface of curvature $R_0$ and then the pressing is released, the cornea is deformed so as to lessen the curvature of the concave curved-surface at the central area of the corneal dome due to the elastically restoring force (spring back) of the eyeball, and thus $R_s$ is set anticipating this spring back amount in advance. As a result, when this spring back amount is defined as $\Delta R$, the curvature $R_s$ is obtained by $R_s = R_0 + \Delta R$.

Specifically, the spring back amount varies by patient and $\Delta R$ is obtained by trial-and-error. However it was found, from treatment cases, that this could be solved by setting $R_s$ to generally satisfy $R_s = R_0 + 5.0$ D to $R_0 + 10.0$ D.

Figure 2:
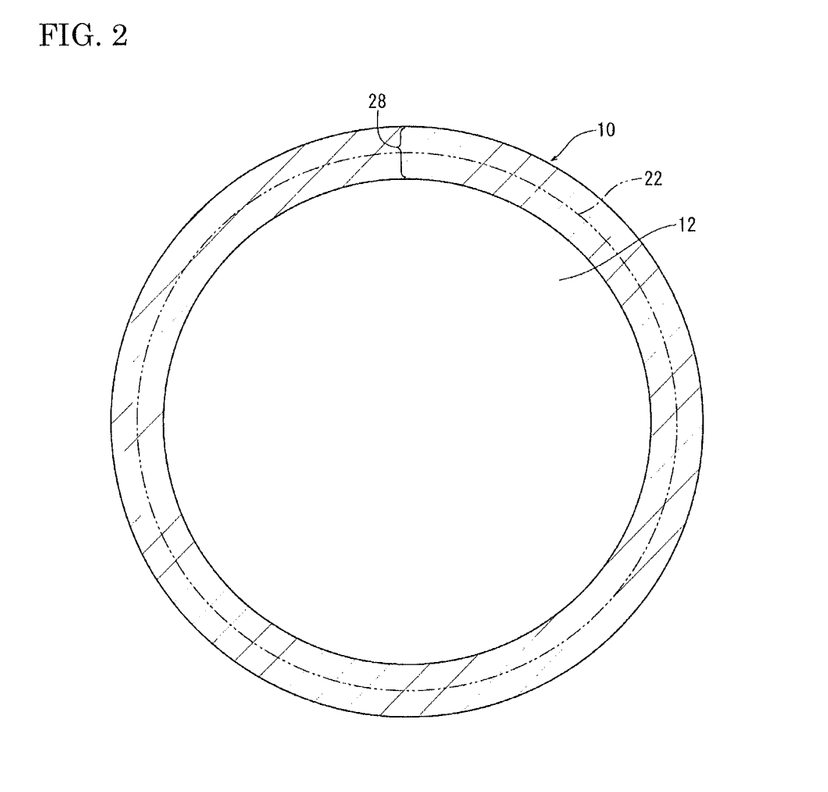
FIG. 2 is a rear view of the contact lens taken along line II-II of FIG. 1.

As shown in FIG. 1 and FIG. 2, an outer diameter $D_1$ of the peripheral portion 26 of the contact lens 10 for correcting myopia is set larger than an average outer diameter $D_0$ of the outer peripheral edge of the human cornea by 3.0 mm to 5.0 mm, and the UV-shielding membrane 28 for shielding ultraviolet rays is provided to the lens in an annular region, on a side in contact with the cornea 12, from a position having a diameter of $D_0$—3.0 mm to $D_0$—5.0 mm to the outermost periphery in the peripheral portion 26. This UV-shielding membrane 28 is preferably made of a material that is harmless even when being in contact with the cornea 12, including, for example, a thin film of gold, titanium, silver, and the like.

As shown in FIG. 2, when the UV-shielding membrane 28 is formed, the peripheral portion 26 of the cornea 12 is not damaged by ultraviolet ray irradiation during crosslinking, thus pluripotent cells for regenerating the cornea can be preserved.

Next, a description will be given of a process for fixing the cornea 12, which is corrected by using the aforementioned contact lens 10 for correcting myopia, by crosslinking.

First, a riboflavin (vitamin B2) solution is infiltrated into the cornea 12 by instillation.

Next, after infiltration of riboflavin, the contact lens 10 for correcting myopia of Example 1 is mounted on the cornea 12 in such a manner that the cornea 12 is pressed by the pressing region 18 located in the center of the lens and a part of the cornea pressed by deformation of the cornea 12 that is pressed enters the relief region 20.

While keeping this state, the cornea 12 is irradiated with ultraviolet rays via the contact lens 10 for correcting myopia, thereby crosslinking collagen fibers that constitute the cornea.

The UV-shielding membrane 28 is formed in the contact lens 10 for correcting myopia on the side in contact with the cornea 12 so as to cover the peripheral portion 26, thus ultraviolet rays do not reach the cornea 12. Thus, pluripotent cells of the cornea 12, localized inside the peripheral portion 26, are not damaged.

Further, even when the contact lens 10 for correcting myopia is removed after completion of the ultraviolet ray irradiation, the cornea 12 is fixed in the same shape as imparted by the pressing region 18 and the relief region 20.

After the contact lens 10 for correcting myopia is removed, the central area of the cornea 12 is projected due to the elastically restoring force of the eyeball. However since the curvature $R_s$ of the convex curved-surface of the pressing region 18 is set anticipating the spring back amount in advance, a curvature of the concave curved-surface formed on the cornea 12 becomes $R_0$ after spring back.

Example 2

Figure 3:
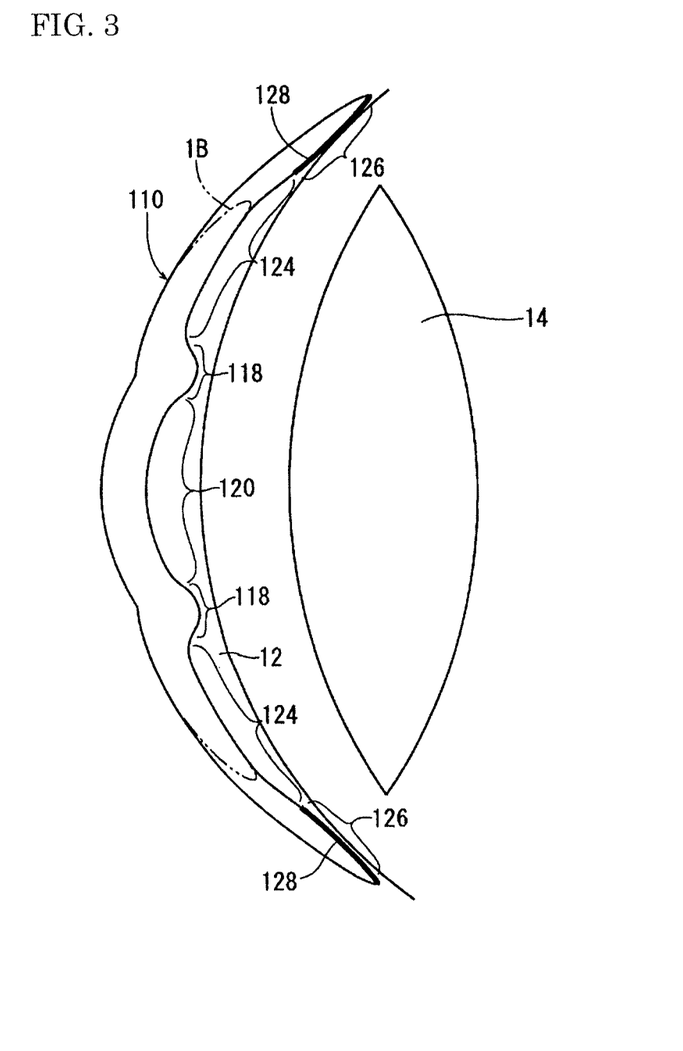
FIG. 3 is a cross-sectional view schematically illustrating a contact lens for corrected-cornea crosslinking according to Example 2 of the present invention.

Next, a contact lens 110 for correcting hyperopia according to Example 2, shown in FIG. 3, will be described. In FIG. 3, a conventional contact lens 1B for correcting hyperopia, shown in FIG. 8, is shown by a two-dot chain line.

The contact lens 110 for correcting hyperopia of Example 2 has a configuration in which a concave part and a convex part are switched between the pressing region and the relief region as compared to the contact lens 10 for correcting myopia shown above in FIG. 1.

In the contact lens 110 for correcting hyperopia, a relief region 120 is formed in a concave curved-surface shape at a position being in contact with the central area of the corneal dome when the lens 110 is mounted on the cornea 12, and a pressing region 118 is constituted by an annular convex portion having a cross section in a convex circular arc shape, the pressing region 118 being formed at a position encircling the outer periphery of the relief region 120.

Furthermore, an anchor region 124 is provided at a position encircling the outer periphery of the pressing region 118 and formed into a shape aligned with a contour of the cornea when the lens 110 is mounted on the cornea 12. A peripheral portion 126 is arranged so as to encircle the outer periphery of the anchor region 124. Reference numeral 128 in FIG. 3 denotes a UV-shielding membrane.

Further, in the contact lens 110 for correcting hyperopia according to Example 2, when a curvature of the convex curved-surface to be formed on the cornea 12 is defined as $r_0$ and a curvature of the concave curved-surface of the relief region 120 is defined as $r_s$ for vision correction, $r_s$ is set to satisfy $r_s=r_0-6.5$ D to $r_0-11.5$ D.

This value is a correction amount obtained by taking into consideration a spring back amount Δr due to the elastically restoring force of the eyeball at the central area of the corneal dome after releasing the pressing force of the contact lens 110 for correcting hyperopia, and is deduced from a large number of treatment cases performed by the inventor. The curvature $r_s$ is obtained as $r_s=r_0-\Delta r$.

When crosslinking is performed to the corrected cornea using the contact lens 110 for correcting hyperopia, crosslinking is performed in the same process as the contact lens 10 for correcting myopia according to the aforementioned Example 1.

Example 3

Figure 4:
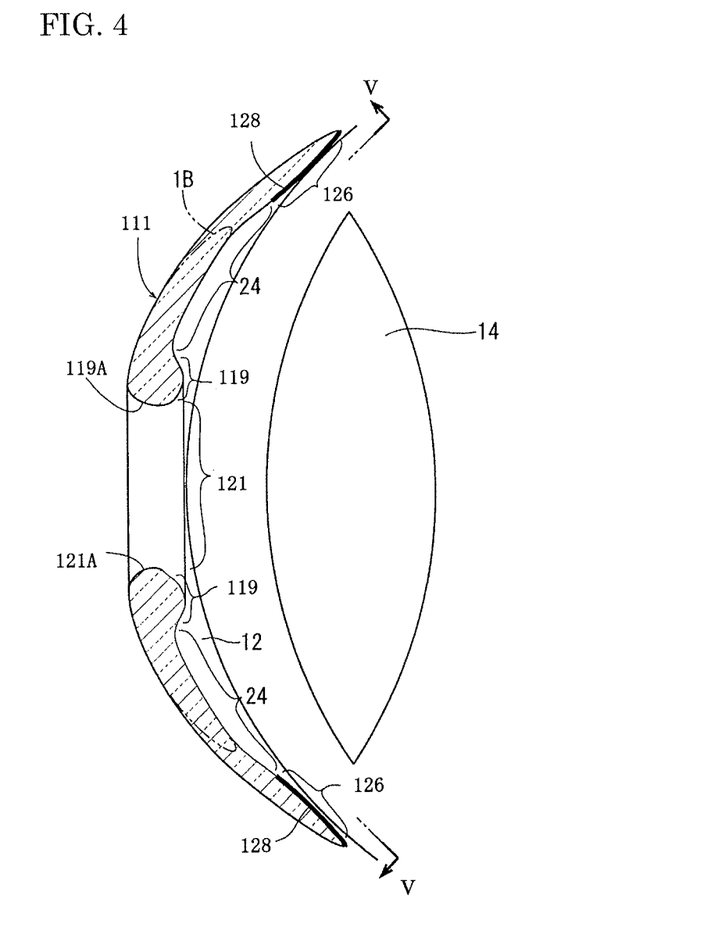
FIG. 4 is a cross-sectional view schematically illustrating a ring-shaped cornea-correction contact lens according to Example 3 of the present invention.

As shown in FIG. 4, a ring-shaped cornea-correction contact lens (hereinafter referred to as a ring-shaped lens) 111 according to Example 3 of the present invention is intended for correcting hyperopia or presbyopia and used by being mounted on a cornea 12.

The ring-shaped lens 111 is configured to include: a relief region 121 formed as a through hole at a position corresponding to the center of a corneal dome (a front end surface of the cornea having the most protruding portion) or the pupil; a pressing region 119 constituted by an annular convex portion having a cross section in a convex circular arc shape on the cornea side, the pressing region 119 being formed at a position encircling the outer periphery of the relief region 121; an anchor region 24 having a shape aligned with a contour 22 (see FIG. 5) of the cornea 12 when the lens is mounted on the cornea 12, the anchor region 24 being provided at a position encircling the outer periphery of the pressing region 20; and a peripheral portion 126 encircling the outer periphery of the anchor region 24.

In the cross section of the ring-shaped lens 111, the pressing region 119 is formed in a convex circular arc shape on the cornea side, and an inner peripheral surface 121A of the through hole as the relief region 121 is smoothly continuous with a convex circular arc 119A of the pressing region 119 and formed in a convex circular arc shape on the center side of the through hole.

In FIG. 4, the conventional lens 1B, shown in FIG. 8, is shown by a two-dot chain line.

Figure 5:
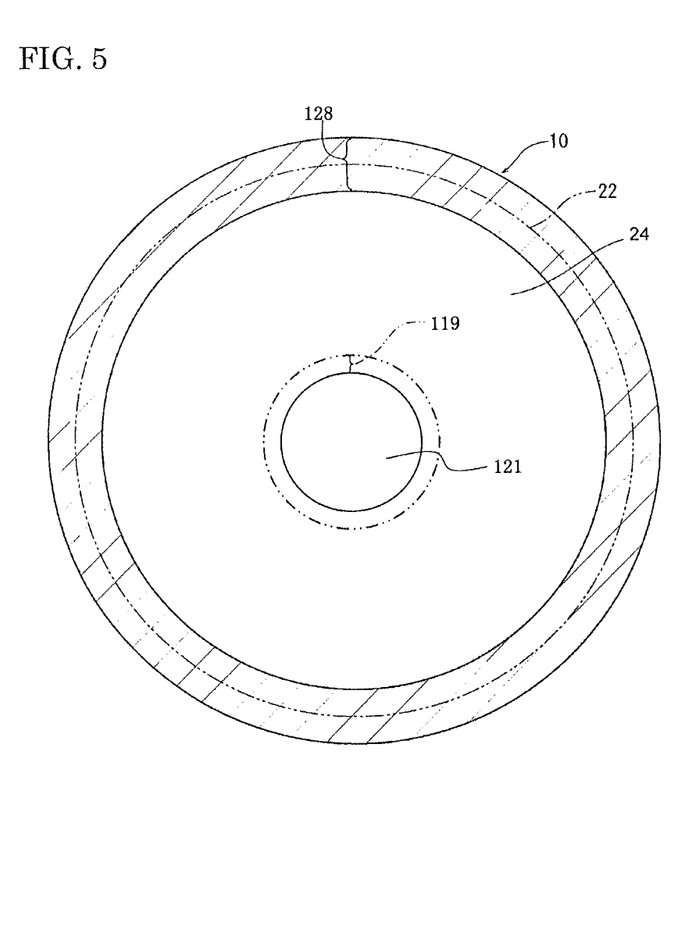
FIG. 5 is a rear view of the contact lens taken along line V-V of FIG. 4.

As shown in FIG. 4 and FIG. 5, an outer diameter $D_1$ of the peripheral portion 126 of the ring-shaped lens 111 is set larger than an average outer diameter $D_0$ of the outer peripheral edge of the human cornea by 3.0 mm to 5.0 mm, and a UV-shielding membrane 28 128 for shielding ultraviolet rays is provided to the lens in an annular region, on the side in contact with the cornea 12, from a position having a diameter of $D_0-3.0$ mm to $D_0-5.0$ mm to the outermost periphery in the peripheral portion 126. This UV-shielding membrane 128 is preferably made of a material that is harmless even when being in contact with the cornea 12, including, for example, a thin film of gold, titanium, silver, and the like.

Correction of hyperopia or presbyopia by the ring-shaped lens 111 of Example 3 is normally performed by wearing the lens during sleep. The ring-shaped lens 10 is pressed by the eyelid during sleep, so that a part of the cornea 12 pressed by the pressing region 119 is pushed into the relief region 121 forming a through hole and, then, the cornea 12 is deformed into a convex lens shape. By performing this process, hyperopia or presbyopia is corrected.

During the correction process mentioned above, since relief region 121 is formed as a through hole, the air and the lacrimal fluid are easily permeated in this part, and thus the cornea can be supplied with oxygen and moistened. Further, the eyelid does not directly touch the ring-shaped lens 111 in the through hole portion and thus easily slides over the ring-shaped lens 111 with less discomfort. Furthermore, as described above, since a part of the cornea 12 pressed by the pressing region 119 is projected into the through hole as the relief region 121, the ring-shaped lens 111 is hardly movable relative to the cornea 12 and can be suppressed from being shifted during sleep.

Further, the ring-shaped lens 111 has the relief region 121 formed as a through hole at a position corresponding to the pupil, and thus one can see things through this through hole in a usual manner and can wear the lens not only during sleep but also in normal daily life conditions.

Next, a description will be given of a process for fixing the cornea 12, which is corrected using the aforementioned ring-shaped lens 111, by crosslinking. In this description, crosslinking refers to a process for fixing the cornea in the corrected state, which is otherwise returned to its original condition of myopia or hyperopia by a restoring force of the cornea when a conventional cornea-correction contact lens is not put on for a long period. This fixing process is performed by irradiating ultraviolet rays on a corneal tissue in a state of being infiltrated with riboflavin (vitamin B2) and crosslinking collagens constituting the cornea to one another.

First, a riboflavin (vitamin B2) solution is infiltrated into the cornea 12 by instillation.

Next, after infiltration of riboflavin, the ring-shaped lens 111 of Example 3 is mounted on the cornea 12 in such a manner that the cornea 12 is pressed by the pressing region 119 and a part of the cornea pressed by deformation of the cornea 12 that is pressed enters the relief region 121 formed as the through hole.

While keeping this state, the cornea 12 is irradiated with ultraviolet rays via the relief region 121 formed as the through hole, thereby crosslinking collagen fibers that constitute the cornea 12.

The UV-shielding membrane 128 is formed in the ring-shaped lens 111 on the side in contact with the cornea 12 so as to cover the peripheral portion 126, and thus ultraviolet rays do not reach the cornea 12. Thus, pluripotent cells of the cornea 12, localized inside the peripheral portion 126, are not damaged.

Further, even when the ring-shaped lens 111 is removed after completion of the ultraviolet ray irradiation, the cornea 12 is fixed in the same shape as imparted by the pressing region 119 and the relief region 121.

It is noted that the ring-shaped lens 111 of the aforementioned Example 3 may be formed transparent using the same material as a conventional contact lens. Furthermore, it may be colored or formed with an opaque material.

Further, it may be considered that the contact lens be produced, for example, by a 3D printer. In this case, even if an ink material is transparent, the lens becomes opaque due to boundaries between granular inks that remain. Thus, in order to make the entire lens transparent, it needs to be subjected to a heat treatment.

The ring-shaped lens of the present invention is formed as a through hole at a position corresponding to the pupil or the central area of the corneal dome when the lens is mounted, therefore allowing its peripheral portions to be opaque. As such, the ring-shaped lens of the present invention does not need to be subjected to a heat treatment or the like after being produced by a 3D printer.

Further, a UV-shielding material (an ultraviolet ray-shielding material) may be used as a material for producing the ring-shaped lens. In this case, the ring-shaped lens 111 may be formed with the UV-shielding material at least in the pressing region 119 or as a whole.

Further, when the ring-shaped lens is used in the above corrected-cornea crosslinking method, only a portion corresponding to the UV-shielding membrane 128 needs to be formed with the UV-shielding material, and when the lens is not used in the crosslinking method, the peripheral portion 126 and the UV-shielding membrane 128 may not be provided.

Example 4

Figure 6:
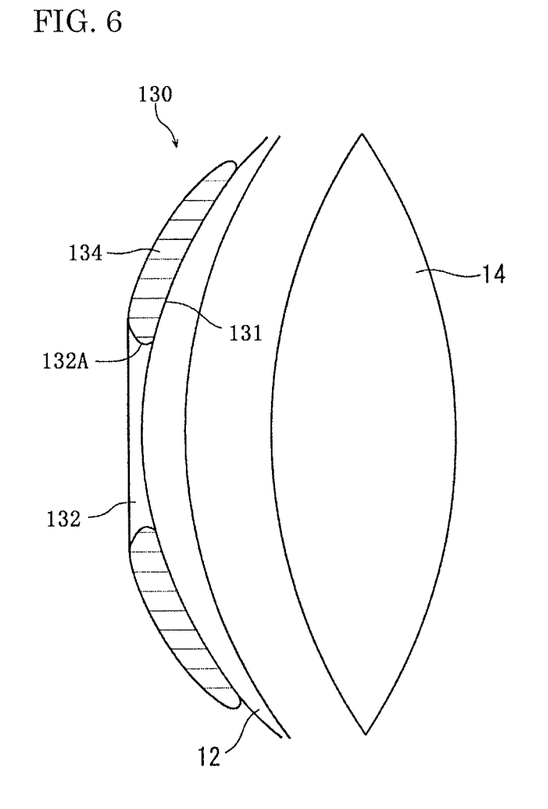
FIG. 6 is a cross-sectional view schematically illustrating Example of a color contact lens for dress up.

Next, Example 4 of the present invention will be described with reference to FIG. 6.

In Example 4, the present invention is applied to a color contact lens for dress up.

This color contact lens for dress up (hereinafter, referred to as a ring-shaped color lens) 130 according to Example 4 is not intended for correcting vision and thus has a simple curved-surface shape along the surface of the cornea 12, where a through hole 132 is formed at a position corresponding to the pupil or the central area of the corneal dome of a wearer and an annular coloring portion 132 is formed at its periphery.

Further, in a cross section of the color lens for dress up 130, an inner peripheral surface 132A of the through hole 132 is continuous with an inside surface 131 of the lens in contact with the cornea 12 and formed in a convex circular arc shape on the center side of the through hole 132.

Accordingly, an end position of the through hole 132 on the side being in contact with the cornea 12 is formed in a circular arc shape, and thus any damage is not given to the cornea 12 or any discomfort is not given to the wearer.

In this ring-shaped color lens 130, a part of the cornea 12 is slightly projected into the through hole 132 side, thus the position of the lens relative to the eyeball is stabilized. Further, as in the case of the ring-shaped lens 111 of Example 3, oxygen and the lacrimal fluid can be supplied inside the through hole 32.

INDUSTRIAL APPLICABILITY

A contact lens for corrected-cornea crosslinking can be used for fixing the cornea by crosslinking in a state that a shape of the cornea is corrected by the contact lens.

REFERENCE SIGNS LIST 1A, 1B conventional lens
10 contact lens for correcting myopia
12 cornea
14 crystalline lens
18, 118, 119 pressing region
20, 120, 121 relief region
22 contour
24, 124 anchor region
26, 126 peripheral portion
28, 128 UV-shielding membrane
110 contact lens for correcting hyperopia
111 ring-shaped cornea-correction contact lens (ring-shaped lens)
130 color contact lens for dress up (ring-shaped color lens)

The invention claimed is:

1. A contact lens for corrected-cornea crosslinking, comprising a relief region constituted by a concave portion and a pressing region constituted by a convex region, each being formed on a side of the contact lens in contact with a cornea of a patient, the contact lens being for correcting at least one of naked eye vision and keratoconus cornea by pressing the relief region and the pressing region in the direction of the cornea and changing a shape thereof, wherein:
when the contact lens is mounted on the cornea, the pressing region is projected in a convex curved-surface shape at a position being in contact with a center of a corneal dome, thereby forming a concave curved-surface on the cornea; and
the relief region is constituted by an annular concave portion that has a cross section in a concave circular arc shape, the relief region being formed at a position encircling an outer periphery of the pressing region, the contact lens further comprising:
an anchor region having a shape aligned with a contour of the cornea when the contact lens is mounted on the cornea, the anchor region being provided at a position encircling an outer periphery of the relief region; and
a peripheral portion encircling an outer periphery of the anchor region, wherein the contact lens is configured such that ultraviolet rays are irradiatable in the contact lens while the contact lens is mounted on the cornea and, when a curvature of the concave curved-surface to be formed on the cornea is defined as $R_O$ and a curvature of the convex curved-surface of the pressing region is defined as $R_S$, the curvature $R_S$ is set to satisfy $R_S=R_O+5.0$ D to $R_O+10.0$ D.

2. The contact lens for corrected-cornea crosslinking according to claim 1, wherein, when the cornea of the patient is pressed by the pressing region of the convex curved-surface and then the pressing is released, and a spring back amount due to an elastically restoring force of an eyeball at the central area of the corneal dome is defined as $\Delta R$, the curvature $R_S$ is obtained by $R_S=R_O+\Delta R$, where $\Delta R$ is within the range of 5.0 D to 10.0 D.

3. A contact lens for corrected-cornea crosslinking, comprising a relief region constituted by a concave portion and a pressing region constituted by a convex region, each being formed on a side of the contact lens in contact with a cornea of a patient, the contact lens being for correcting at least one of naked eye vision and keratoconus cornea by pressing the relief region and the pressing region in the direction of the cornea and changing a shape thereof, wherein:
when the contact lens is mounted on the cornea, the relief region is formed in a concave curved-surface shape at a position corresponding to a center of a corneal dome, thereby forming a convex curved-surface on the cornea; and
the pressing region is constituted by an annular convex portion that has a cross section in a convex circular arc shape, the pressing region being formed at a position encircling an outer periphery of the relief region and in contact with a non-central portion of the cornea, the contact lens further comprising:
an anchor region having a shape aligned with a contour of the cornea when the contact lens is mounted on the cornea, the anchor region being provided at a position encircling an outer periphery of the pressing region; and a peripheral portion encircling an outer periphery of the anchor region, wherein the contact lens is configured such that ultraviolet rays are irradiatable in the contact lens while the contact lens is mounted on the cornea and, when the curvature of the convex curved-surface to be formed on the cornea is defined as $r_0$ and a curvature of the concave curved-surface of the relief region is defined as $r_S$, the curvature $r_S$ is set to satisfy $r_S=r_0+\Delta r$, where $\Delta r$ is within the range of −6.5 D to −11.5 D.

4. The contact lens for corrected-cornea crosslinking according to claim 3, wherein, when the cornea of the patient is pressed by the relief region of the concave curved-surface and then the pressing is released after crosslinking, and a spring back amount due to an elastically restoring force of an eyeball at the central area of the corneal dome is defined as $\Delta r$, the curvature $r_S$ is obtained by $r_S=r_0+\Delta r$, where $\Delta r$ is within the range of −6.5 D to −11.5 D.

5. The contact lens for corrected-cornea crosslinking according to claim 1, wherein an outer diameter $D_1$ of the peripheral portion is set larger than an average outer diameter $D_0$ of an outer peripheral edge of a human cornea by 3.0 mm to 5.0 mm, and a UV-shielding membrane for shielding ultraviolet rays is provided to the lens in an annular region, on a side in contact with the cornea, from a position having a diameter of $D_0$−3.0 mm to $D_0$−5.0 mm to an outermost periphery in the peripheral portion.

6. The contact lens for corrected-cornea crosslinking according to claim 2, wherein an outer diameter $D_1$ of the peripheral portion is set larger than an average outer diameter $D_0$ of an outer peripheral edge of a human cornea by 3.0 mm to 5.0 mm, and a UV-shielding membrane for shielding ultraviolet rays is provided to the lens in an annular region, on a side in contact with the cornea, from a position having a diameter of $D_0$−3.0 mm to $D_0$−5.0 mm to an outermost periphery in the peripheral portion.

7. The contact lens for corrected-cornea crosslinking according to claim 3, wherein an outer diameter $D_1$ of the peripheral portion is set larger than an average outer diameter $D_0$ of an outer peripheral edge of a human cornea by 3.0 mm to 5.0 mm, and a UV-shielding membrane for shielding ultraviolet rays is provided to the lens in an annular region, on a side in contact with the cornea, from a position having a diameter of $D_0$−3.0 mm to $D_0$−5.0 mm to an outermost periphery in the peripheral portion.

8. The contact lens for corrected-cornea crosslinking according to claim 4, wherein an outer diameter $D_1$ of the peripheral portion is set larger than an average outer diameter $D_0$ of an outer peripheral edge of a human cornea by 3.0 mm to 5.0 mm, and a UV-shielding membrane for shielding ultraviolet rays is provided to the lens in an annular region, on a side in contact with the cornea, from a position having a diameter of $D_0$−3.0 mm to $D_0$−5.0 mm to an outermost periphery in the peripheral portion.

9. A corrected-cornea crosslinking method comprising:
a step of infiltrating a riboflavin solution into a corneal tissue;
a step of mounting the contact lens for corrected-cornea crosslinking according to claim 1 on the cornea after infiltration of the riboflavin in such a manner that the cornea is pressed by the pressing region and a part of the cornea pressed by deformation of the cornea that is pressed enters the relief region; and
a step of irradiating, while the contact lens for corrected-cornea crosslinking is mounted on the cornea, the cornea with ultraviolet rays via the contact lens for corrected-cornea crosslinking, thereby crosslinking collagen fibers that constitute the cornea.

10. A ring-shaped cornea-correction contact lens, comprising a relief region constituted by a through hole and a pressing region constituted by a convex region, each being formed on a side of the contact lens in contact with a cornea of a patient, the cornea-correction contact lens being for correcting at least one of hyperopia or presbyopia by pressing at least the pressing region to the cornea and changing a shape thereof, wherein:
when the contact lens is mounted on the cornea, the relief region is formed as a through hole at a position corresponding to a central area of a corneal dome, so that the cornea is projected into the through hole to form a convex curved-surface; and
the pressing region is constituted by an annular convex portion having a cross section in a convex circular arc shape, the pressing region being formed at a position encircling an outer periphery of the relief region, the cornea-correction contact lens further comprising at least an anchor region having a shape aligned with a contour of the cornea when the lens is mounted on the cornea, the anchor region being provided at a position encircling an outer periphery of the pressing region; and a peripheral portion encircling an outer periphery of the anchor region,
the peripheral portion which includes the outer periphery of the anchor region and of which outer diameter $D_1$ is set larger than an average outer diameter $D_0$ of an outer peripheral edge of a human cornea by 3.0 mm to 5.0 mm; and a UV-shielding membrane for shielding ultraviolet rays provided to the lens in an annular region, on a side in contact with the cornea, from a position having a diameter of $D_0$−3.0 mm to $D_0$−5.0 mm to an outermost periphery in the peripheral portion.

11. A corrected-cornea crosslinking method comprising:
a step of infiltrating a riboflavin solution into a corneal tissue;
a step of mounting the ring-shaped cornea-correction contact lens according to claim 3 on the cornea after infiltration of the riboflavin in such a manner that the cornea is pressed by the pressing region and a part of the cornea pressed by deformation of the cornea that is pressed enters the relief region; and
a step of irradiating, while the ring-shaped cornea-correction contact lens is mounted on the cornea, the cornea with ultraviolet rays via the through hole, thereby crosslinking collagen fibers that constitute the cornea.

* * * * *